(12) United States Patent
Stigall et al.

(10) Patent No.: US 11,419,580 B2
(45) Date of Patent: Aug. 23, 2022

(54) DISPOSABLE THERAPEUTIC ULTRASOUND DEVICE

(71) Applicant: KONINKLIJKE PHILIPS N.V., Eindhoven (NL)

(72) Inventors: Jeremy Stigall, Carlsbad, CA (US); Princeton Saroha, Ladera Ranch, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 705 days.

(21) Appl. No.: 15/999,189

(22) Filed: Aug. 15, 2018

(65) Prior Publication Data
US 2019/0053787 A1    Feb. 21, 2019

Related U.S. Application Data

(60) Provisional application No. 62/546,184, filed on Aug. 16, 2017.

(51) Int. Cl.
*A61B 8/00* (2006.01)
*A61B 17/22* (2006.01)
(Continued)

(52) U.S. Cl.
CPC ........ *A61B 8/4494* (2013.01); *A61B 5/02007* (2013.01); *A61B 8/12* (2013.01);
(Continued)

(58) Field of Classification Search
CPC ............ A61B 8/4494; A61B 17/22012; A61B 5/02007; A61B 8/12; A61B 8/469;
(Continued)

(56) References Cited

U.S. PATENT DOCUMENTS 6,200,268 B1    3/2001   Vince
6,381,350 B1    4/2002   Klingensmith
(Continued)

FOREIGN PATENT DOCUMENTS

WO    2013165935 A1   11/2013

OTHER PUBLICATIONS

Stigall, Jeremy et al. Intraluminal Ultrasound Device for Diagnositc Imaging and Therapy U.S. Appl. No. 62/545,944, filed Aug. 15, 2017.

*Primary Examiner* — Joel Lamprecht

(57) ABSTRACT

Therapeutic ultrasound devices and methods are provided. In one embodiment, a therapeutic ultrasound device includes a housing configured for handheld operation by a user, an ultrasound assembly positioned within the housing and configured to generate ultrasound energy, a battery positioned in the housing and coupled to the ultrasound assembly to power the ultrasound assembly to generate the ultrasound energy, a flexible elongate member configured to be positioned within a body lumen of a patient, and an acoustic transmission member. The flexible elongate member includes a proximal portion, a distal portion, and a first lumen extending between the proximal portion and the distal portion. The housing is coupled to the proximal portion. The acoustic transmission member includes a proximal portion acoustically coupled to the ultrasound assembly and configured to receive the ultrasound energy, and a distal portion extending within the first lumen and configured to transmit the ultrasound energy to the body lumen to deliver a therapy.

17 Claims, 8 Drawing Sheets

(51) Int. Cl.
  *A61N 7/02* (2006.01)
  *A61B 5/02* (2006.01)
  *A61B 8/12* (2006.01)
  *A61B 8/08* (2006.01)
  *B06B 1/06* (2006.01)
  *G06T 7/00* (2017.01)

(52) U.S. Cl.
  CPC ............ *A61B 8/469* (2013.01); *A61B 8/5238* (2013.01); *A61B 17/22012* (2013.01); *A61N 7/022* (2013.01); *B06B 1/06* (2013.01); *G06T 7/0012* (2013.01); *A61B 2017/22001* (2013.01); *A61B 2017/22008* (2013.01); *A61B 2017/22014* (2013.01); *G06T 2207/10132* (2013.01); *G06T 2207/30101* (2013.01)

(58) Field of Classification Search
  CPC ........ A61B 8/5238; A61B 2017/22008; A61B 2017/22001; A61B 2017/22014; A61N 7/022; B06B 1/06; G06T 7/0012; G06T 2207/10132; G06T 2207/30101
  See application file for complete search history.

(56) References Cited

U.S. PATENT DOCUMENTS

| | | | |
|---|---|---|---|
| 6,551,337 | B1 | 4/2003 | Rabiner |
| 7,074,188 | B2 | 7/2006 | Nair |
| 7,175,597 | B2 | 2/2007 | Vince |
| 7,215,802 | B2 | 5/2007 | Klingensmith |
| 7,359,554 | B2 | 4/2008 | Klingensmith |
| 7,431,728 | B2 | 10/2008 | Gerry |
| 7,463,759 | B2 | 12/2008 | Klingensmith |
| 8,784,356 | B2 | 7/2014 | Sliwa |
| 2007/0085611 | A1* | 4/2007 | Gerry ............... A61B 17/22012 331/16 |
| 2009/0163940 | A1* | 6/2009 | Sliwa ............... A61B 17/22012 606/159 |

* cited by examiner

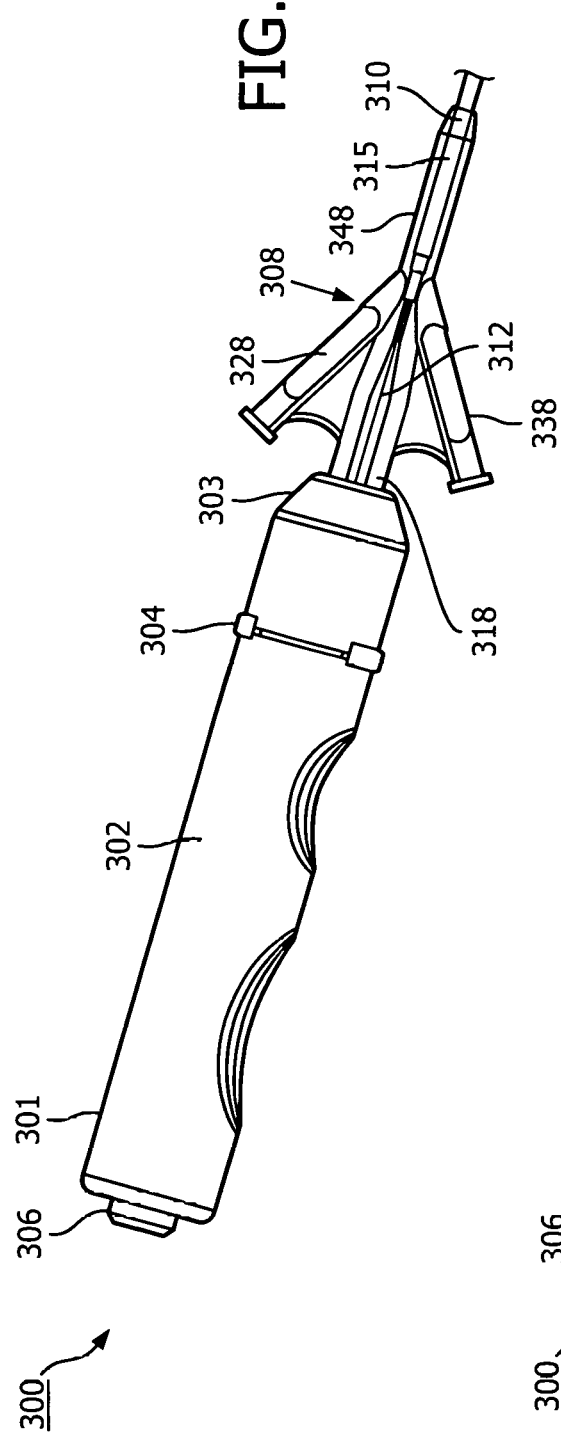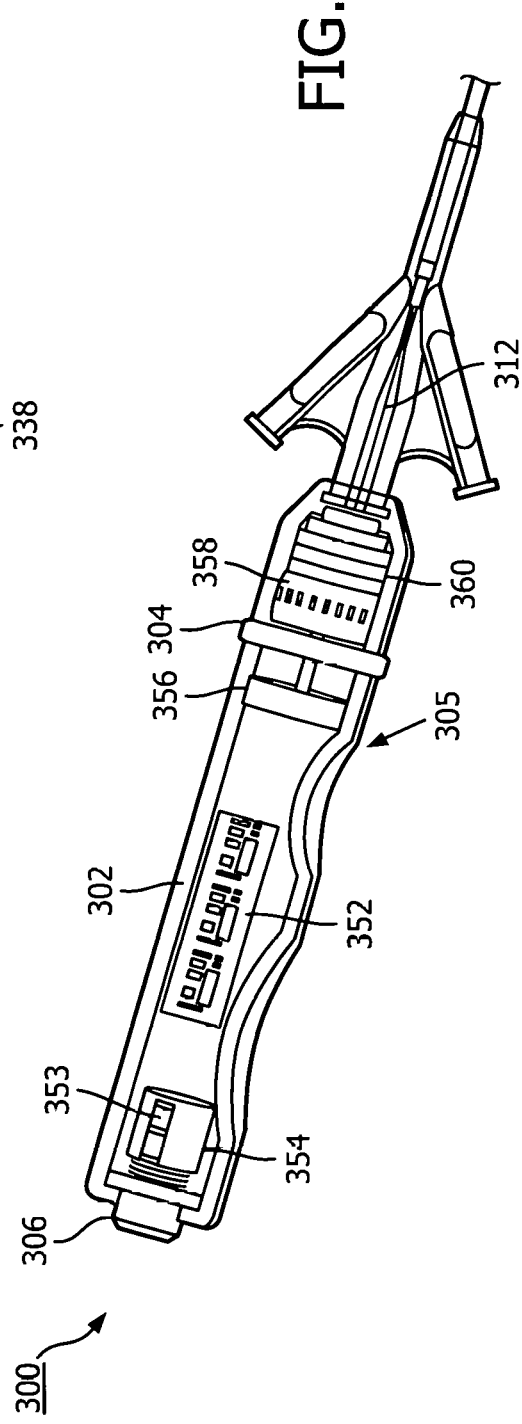

DISPOSABLE THERAPEUTIC ULTRASOUND DEVICE

CROSS-REFERENCE TO RELATED APPLICATION

The present application claims priority to and the benefit of U.S. Provisional Application No. 62/546,184, filed Aug. 16, 2017, the entirety of which is hereby incorporated by reference herein.

TECHNICAL FIELD

The present disclosure relates generally to treating an anatomy of a patient or preparing the anatomy of the patient for a pharmacological treatment. Specifically, the disclosure relates to a self-contained and disposable therapeutic intraluminal ultrasound device.

BACKGROUND

Angioplasty is commonly performed using the following technologies: balloons (standard and drug coated), stents (bare metal, drug eluting, bioresorbable), aspiration catheters, and atherectomy. Aside from minimally invasive surgical intervention, other common methods include open heart surgery and anticoagulation regimens. Ultrasound has been used in variety of intraluminal therapies, including aspiration, ultrasonic vessel preparation, lithotripsy, ultrasonic thrombectomy, balloon angioplasty, localized drug delivery, and enhanced drug delivery. Conventionally, intraluminal ultrasound therapeutic devices have to be coupled to an external system and rely on the external system as a power source, a signal source, and/or an external ultrasound generator. Such external systems can be costly, as well as bulky, taking up valuable space in a procedure room and limiting mobility. The therapeutic devices also require a wired connection to external system for power, signal, and/or ultrasound transmission, which further reduces a clinician's ability to maneuver the device as needed.

SUMMARY

Embodiments of the present disclosure provide a self-contained and disposable therapeutic intraluminal ultrasound device. For example, the therapeutic intraluminal ultrasound device includes an ultrasound assembly, a flexible elongate member, an acoustic transmission member, a battery, and a housing sized and shaped for handheld operation by a user. The housing houses the ultrasound assembly and the battery that powers the ultrasound assembly to generate ultrasound energy. A proximal portion of the flexible elongate member is coupled to the housing. The acoustic transmission member is coupled to the ultrasound assembly and extends through a lumen within the flexible elongate member. The therapeutic intraluminal ultrasound device can be used to deliver a therapy to a body lumen of a patient when the flexible elongate member is positioned within the body lumen. The systems, devices and methods described herein advantageously do away with costly and bulky external systems and introduce mobility, versatility and availability to intraluminal ultrasound therapy through a self-contained therapeutic intraluminal ultrasound device.

In one embodiment, a therapeutic intraluminal ultrasound device is provided. The therapeutic intraluminal ultrasound device includes a housing configured for handheld operation by a user, an ultrasound assembly positioned within the housing and configured to generate ultrasound energy, a battery positioned in the housing and coupled to the ultrasound assembly to power the ultrasound assembly to generate the ultrasound energy, a flexible elongate member configured to be positioned within a body lumen of a patient, and an acoustic transmission member. The flexible elongate member includes a proximal portion, a distal portion, and a first lumen extending between the proximal portion and the distal portion. The housing is coupled to the proximal portion. The acoustic transmission member includes a proximal portion acoustically coupled to the ultrasound assembly and configured to receive the ultrasound energy; and a distal portion extending within the first lumen and configured to transmit the ultrasound energy to the body lumen to deliver a therapy.

In some embodiments, the ultrasound assembly includes an ultrasound amplifier. In some implementations, the ultrasound assembly comprises a piezoelectric micromachined ultrasound transducer (PMUT), a capacitive micromachined ultrasound transducer (CMUT), a lead zirconate titanate (PZT) transducer, a PZT composite transducer, or a combination thereof. In some implementations, the ultrasound assembly includes a backing plate positioned proximal to the ultrasound amplifier. The proximal portion of the acoustic transmission member extends through a through hole within the ultrasound amplifier and is partially received within a recess in the backing plate, thereby acoustically coupled to the ultrasound assembly. In some embodiments, the ultrasound assembly includes a stack of a plurality of piezoelectric components positioned around a circumference of the ultrasound amplifier. In some instances, each of the plurality of piezoelectric components is donut-shaped and includes a center frequency different from another of the plurality of piezoelectric components. In some implementations, the ultrasound assembly includes a tunable center frequency range between 1 kHz and 5 MHz.

In some embodiments, the therapeutic intraluminal ultrasound device further includes a switch positioned on the housing and the switch is configured to, when switched on, turn on the ultrasound assembly. In some implementations, the housing further includes a hub and is coupled to the proximal portion of the flexible elongate member via the hub. In some instances, the therapeutic intraluminal ultrasound device further includes a first access port coupled to the hub. The first access port includes an access lumen in fluid communication with the first lumen of the flexible elongate member. In some embodiments, the therapeutic intraluminal ultrasound device further includes a second access port coupled to the hub. The second access port includes an access lumen in fluid communication with a second lumen of the flexible elongate member. The second lumen extends between the proximal portion and the distal portion of the flexible elongate member and parallel to the first lumen. In some implementations, the therapeutic intraluminal ultrasound device further includes a coupling component proximal to the hub and configured to acoustically couple the acoustic transmission member. In those implementations, the coupling component includes a collet head, an O-ring, a clamp, or a keyed interface.

In another embodiment, a method for intraluminal ultrasound therapy is provided. The method includes positioning, within a body lumen of a patient, a flexible elongate member of a therapeutic intraluminal ultrasound device. The therapeutic intraluminal ultrasound device includes a housing configured for handheld operation by a user, an ultrasound assembly positioned within the housing and configured to generate ultrasound energy, a battery positioned in the housing and coupled to the ultrasound assembly to power the ultrasound assembly to generate the ultrasound energy, the flexible elongate member, and an acoustic transmission member. The flexible elongate member includes a proximal portion, a distal portion, and a first lumen extending between the proximal portion and the distal portion. The housing is coupled to the proximal portion. The acoustic transmission member includes a proximal portion acoustically coupled to the ultrasound assembly and configured to receive the ultrasound energy, and a distal portion extending within the first lumen and configured to transmit the ultrasound energy to the body lumen. The method includes applying a therapy to the body lumen of the patient by activating the ultrasound assembly.

In some embodiments, applying the therapy to the body lumen of the patient comprises turning on a switch positioned on the housing of the therapeutic intraluminal ultrasound device. In some embodiments, the method further includes prior to positioning, within the body lumen of the patient, the flexible elongate member of the therapeutic intraluminal ultrasound device, interrogating the body lumen with a diagnostic device to obtain information for the therapy. In some embodiments, the method further includes, prior to positioning, within the body lumen of the patient, the flexible elongate member of the therapeutic intraluminal ultrasound device, coupling the acoustic transmission member to the ultrasound assembly.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIGS. 3A-3D are diagrammatic schematic views of a therapeutic ultrasound device according to embodiments of the present disclosure.

DETAILED DESCRIPTION

Figure 1:
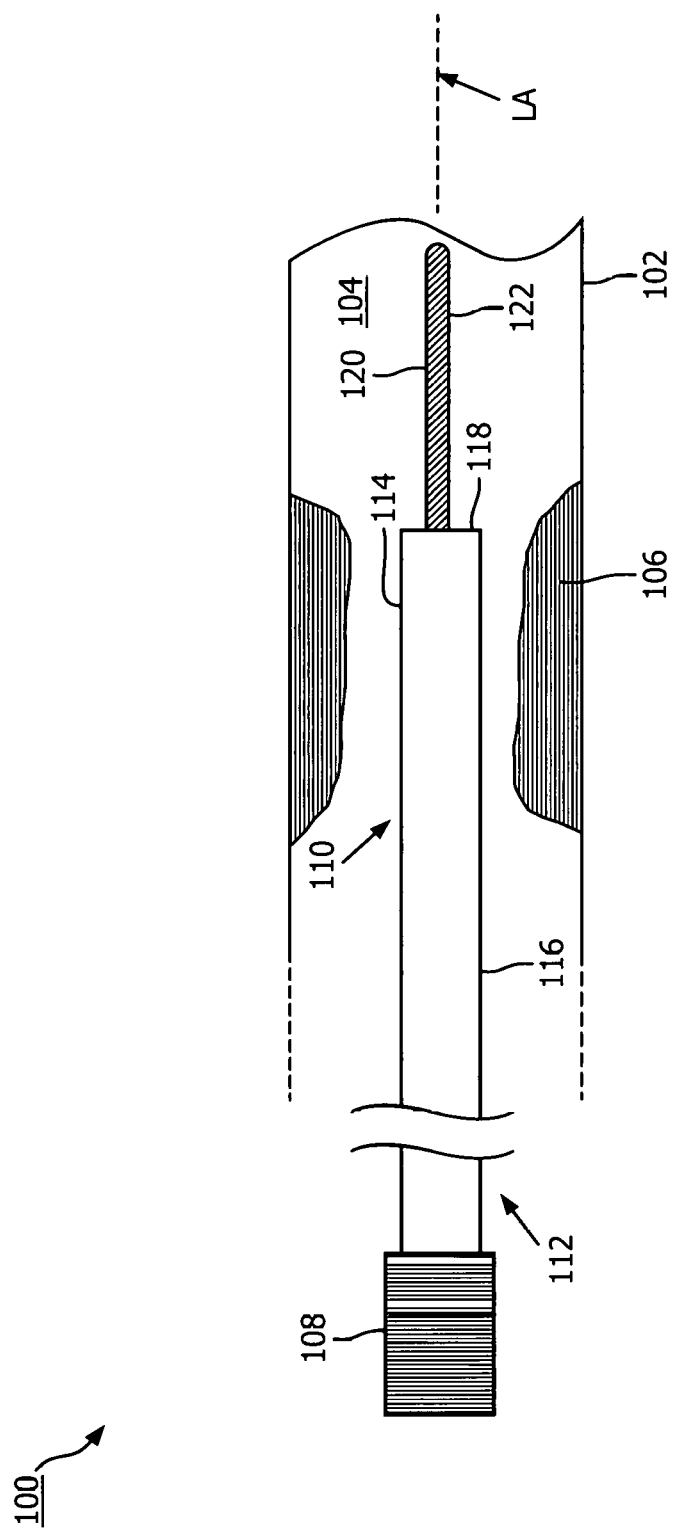
FIG. 1 is a diagrammatic schematic view of a therapeutic ultrasound device according to some embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of a therapeutic ultrasound device 100 according to some embodiments of the present disclosure. The therapeutic ultrasound device 100 can include a housing 108, a flexible elongate member 110, and an acoustic transmission member 120. The housing 108 is configured (or sized and shaped, or structurally arranged) for handheld operation by a user and can therefore be referred to as the handle 108 as well. As will be described in more detail in conjunction with FIGS. 3A, 3B and 4, the housing 108 may house an ultrasound assembly and a battery. The ultrasound assembly may include an ultrasound amplifier, a stack of piezoelectric components positioned around a circumference of the ultrasound amplifier, a backing plate, and a driving circuit. The battery may be secured in a battery harness and coupled to the ultrasound assembly. In some embodiments, the housing 108 may include a switch that includes a button on the housing 108. Activation of the switch, by, for example, pushing the button, can cause the driving circuit to energize the piezoelectric components to emit ultrasound energy. The flexible elongate member 110 and/or the device 100 can be referenced as a catheter. The flexible elongate member 110 includes a proximal portion 112 and a distal portion 114. At least a portion the proximal portion 112 of the flexible elongate member 110 is coupled to the housing 108. As will be described in more detail in conjunction with FIGS. 3A, 3B and 4, the acoustic transmission member 120 extends within a lumen of the flexible elongate member 110. The lumen extends between the proximal portion 112 and the distal portion 114. In some implementations, the proximal portion of the acoustic transmission member 120 is received within a recess on the backing plate and a through hole within the ultrasound amplifier. In some embodiments, the acoustic transmission member 120 may serve as an intermediate member or a coupling member that couples to a radiating member via a distal portion 122 of the acoustic transmission member 120.

As used herein, "elongate member" or "flexible elongate member," such as the flexible elongate member 110, includes at least any thin, long, flexible structure structurally arranged (e.g., sized and/or shaped) to be positioned within a body lumen (or lumen) 104 of the anatomy 102. For example, a distal portion 114 of the flexible elongate member 110 is positioned within the lumen 104, while a proximal portion 112 of the flexible elongate member 110 is positioned outside of the body of the patient. The flexible elongate member 110 can include a longitudinal axis LA. In some instances, the longitudinal axis LA can be a central longitudinal axis of the flexible elongate member 110. In some embodiments, the flexible elongate member 110 can include one or more polymer/plastic layers formed of various grades of nylon, Pebax, polymer composites, polyimides, and/or Teflon. In some embodiments, the flexible elongate member 110 can include one or more layers of braided metallic and/or polymer strands. The braided layer(s) can be tightly or loosely braided in any suitable configuration, including any suitable per in count (pic). In some embodiments, the flexible elongate member 110 can include one or more metallic and/or polymer coils. All or a portion of the flexible elongate member 110 may have any suitable geometric cross-sectional profile (e.g., circular, oval, rectangular, square, elliptical, etc.) or non-geometric cross-sectional profile. For example, the flexible elongate member 110 can have a generally cylindrical profile with a circular cross-sectional profile that defines an outer diameter of the flexible elongate member 110. For example, the outer diameter of the flexible elongate member 110 can be any suitable value for positioning within the anatomy 102, including between approximately 1 Fr (0.33 mm) and approximately 15 Fr (5 mm), including values such as 3.5 Fr, 5 Fr, 7 Fr, 8.2 Fr, 9 Fr, and/or other suitable values both larger and smaller.

The flexible elongate member 110 may include one or more lumens extending along all or a portion of the length of the flexible elongate member 110, such as the lumen in which the acoustic transmission member 120 extends. The lumen(s) of the ultrasound device 100 can be structurally arranged (e.g., sized and/or shaped) to receive and/or guide one or more other diagnostic and/or therapeutic instruments—such as the acoustic transmission member 120, an inflation line for balloon angioplasty, or a drug delivery line. The lumen(s) may be centered or offset with respect to the cross-sectional profile of the flexible elongate member 110. In some implementations, one or more of the lumen(s) of the flexible elongate member 110 may be in fluid communication with one or more port on the housing. The one or more port can be an access port(s) for a vacuum line(s) for aspiration, a drug delivery line(s) for drug delivery, or an inflation line(s) for balloon angioplasty. In some embodiments, one of the lumen(s) may be a guide wire lumen to receive and ride on a guide wire. Generally, the guide wire is a thin, long, flexible structure that is structurally arranged (e.g., sized and/or shaped) to be disposed within the lumen 104 of the anatomy 102. During a diagnostic and/or therapeutic procedure, a medical professional typically first inserts the guide wire into the lumen 104 of the anatomy 102 and moves the guide wire to a desired location within the anatomy 102, such as adjacent to an occlusion 106. The guide wire facilitates introduction and positioning of one or more other diagnostic and/or therapeutic instruments, including the flexible elongate member 110 of the therapeutic ultrasound device 100, at the desired location within the anatomy 102. In some embodiments, the therapeutic ultrasound device 100 is not used with a guide wire.

The anatomy 102 may represent any fluid-filled or surrounded structures, both natural and man-made. For example, the anatomy 102 can be within the body of a patient. Fluid can flow through the lumen 104 of the anatomy 102. In some instances, the therapeutic ultrasound device 100 can be referenced as an intraluminal device. The anatomy 102 can be a vessel, such as a blood vessel, in which blood flows through the lumen 104. In some instances, the therapeutic ultrasound device 100 can be referenced as an intravascular device. In various embodiments, the blood vessel is an artery or a vein of a patient's vascular system, including cardiac vasculature, peripheral vasculature, neural vasculature, renal vasculature, and/or any other suitable anatomy/lumen inside the body. The anatomy 102 can be tortuous in some instances. For example, the therapeutic ultrasound device 100 may be used to deliver a therapy any number of anatomical locations and tissue types, including without limitation, organs including the liver, heart, kidneys, gall bladder, pancreas, lungs, esophagus; ducts; intestines; nervous system structures including the brain, dural sac, spinal cord and peripheral nerves; the urinary tract; as well as valves within the blood, chambers or other parts of the heart, and/or other systems of the body. In those examples, the therapeutic ultrasound device 100 may be used to prepare those anatomical locations for a therapy. In addition to natural structures, the therapeutic ultrasound device 100 may be used to deliver therapy to anatomies adjacent or around man-made structures such as, but without limitation, heart valves, stents, shunts, filters and other devices.

The occlusion 106 of the anatomy 102 is generally representative of any blockage or other structural arrangement that results in a restriction to the flow of fluid through the lumen 104, for example, in a manner that is deleterious to the health of the patient. For example, the occlusion 106 narrows the lumen 104 such that the cross-sectional area of the lumen 104 and/or the available space for fluid to flow through the lumen 104 is decreased. Where the anatomy 102 is a blood vessel, the occlusion 106 may be a result of plaque buildup, including without limitation plaque components such as fibrous, fibro-lipidic (fibro fatty), necrotic core, calcified (dense calcium), blood, fresh thrombus, and/or mature thrombus. In some instances, the occlusion 106 can be referenced as thrombus, a stenosis, and/or a lesion. Generally, the composition of the occlusion 106 will depend on the type of anatomy being evaluated. Healthier portions of the anatomy 102 may have a uniform or symmetrical profile (e.g., a cylindrical profile with a circular cross-sectional profile). The occlusion 106 may not have a uniform or symmetrical profile. Accordingly, diseased portions of the anatomy 102, with the occlusion 106, will have a non-symmetric and/or otherwise irregular profile. While the anatomy 102 is illustrated in FIG. 1 as having a single occlusion 106, it is understood that the devices, systems, and methods described herein have similar application for anatomy having multiple occlusions.

The ultrasound assembly in the housing 108 may include a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In some implementations, the ultrasound assembly may include a transducer that includes a plurality of piezoelectric components. Depending on the transducer material, the manufacturing process for the piezoelectric components can include dicing, kerfing, grinding, sputtering, wafer technologies (e.g., SMA, sacrificial layer deposition), other suitable processes, and/or combinations thereof. In some implementations, the center frequencies of the ultrasound assembly can be between 1 kHz and 5 MHz, for example, including values such as 50 kHz, 500 kHz, 1 MHz, 3 MHz, and/or other suitable values both larger and smaller. In some embodiments, the center frequency of the ultrasound assembly is tunable. For example, the ultrasound assembly can include a stack of piezoelectric components of different dimensions and therefore, of different center frequencies. By selectively activating one of the piezoelectric components, the ultrasound assembly operates at the center frequency of the activated piezoelectric component. In some instances, each of the piezoelectric components in the stack is disk-shaped. Because each of the piezoelectric components are sized and shaped to be positioned around a circumference of an ultrasound amplifier, each of the disk-shaped piezoelectric components has a through hole. For that reason, each of the piezoelectric components is donut-shaped. For another example, the frequency of the ultrasonic energy emitted by the ultrasound assembly can be modified by the voltage of the applied electrical signal and/or the application of a biasing voltage to the piezoelectric component(s). The electrical signal is supplied by a driving circuit coupled to a battery. In some implementations, the driving circuit is an application specific integrated circuit (ASIC).

In some embodiments, the therapeutic ultrasound device 100 is configured to apply an ultrasound therapy to the anatomy 102, such as the occlusion 106. For example, via the acoustic transmission member 120, the therapeutic ultrasound device 100 emits sound waves that damage the structure of the occlusion 106. In that regard, the therapeutic ultrasound device 100 can be referenced as a lithotripsy device. The ultrasonic energy emitted by the therapeutic ultrasound device 100 through the acoustic transmission member 120 can create micro fractures in the occlusion 106. For example, the acoustic transmission member by itself or by a radiating member coupled to the acoustic transmission member 120 can deliver ultrasonic energy in a targeted manner to cause cavitation (e.g., wave force cavitation, thermal cavitation, etc.) of the occlusion 106. Delivery of ultrasound therapy by the acoustic transmission member 120 (or the radiating member coupled to the acoustic transmission member 120) advantageously facilitates thrombus dilution and/or vessel preparation. For example, ultrasound therapy can be applied prior to delivery of a pharmacological agent to the anatomy 102. The pharmacological agent can be a thrombolytic agent, a fibrinolytic agent, plasmin, plasmid, tissue plasminogen activator, urokinase, streptokinase, collagenace, hepranoid, anti-thrombin drug, any other suitable drug, and/or combinations thereof. As described herein, Pharmacological uptake can be advantageously improved as a result of the degradation of the occlusion 106 by the ultrasonic energy. By compromising the structure of the occlusion 106, additional surface area is available for the pharmacological agent to contact and/or penetrate the anatomy 102. Accordingly, the efficacy of the treatment and the health of the patient are improved. In some embodiments, the pharmacological agent can be delivered through a drug delivery port in fluid communication with a lumen within the flexible elongate member 110. In some instances, the drug delivery port and the acoustic transmission member 120 share the same lumen that extends within the flexible elongate member 110.

Figure 2:
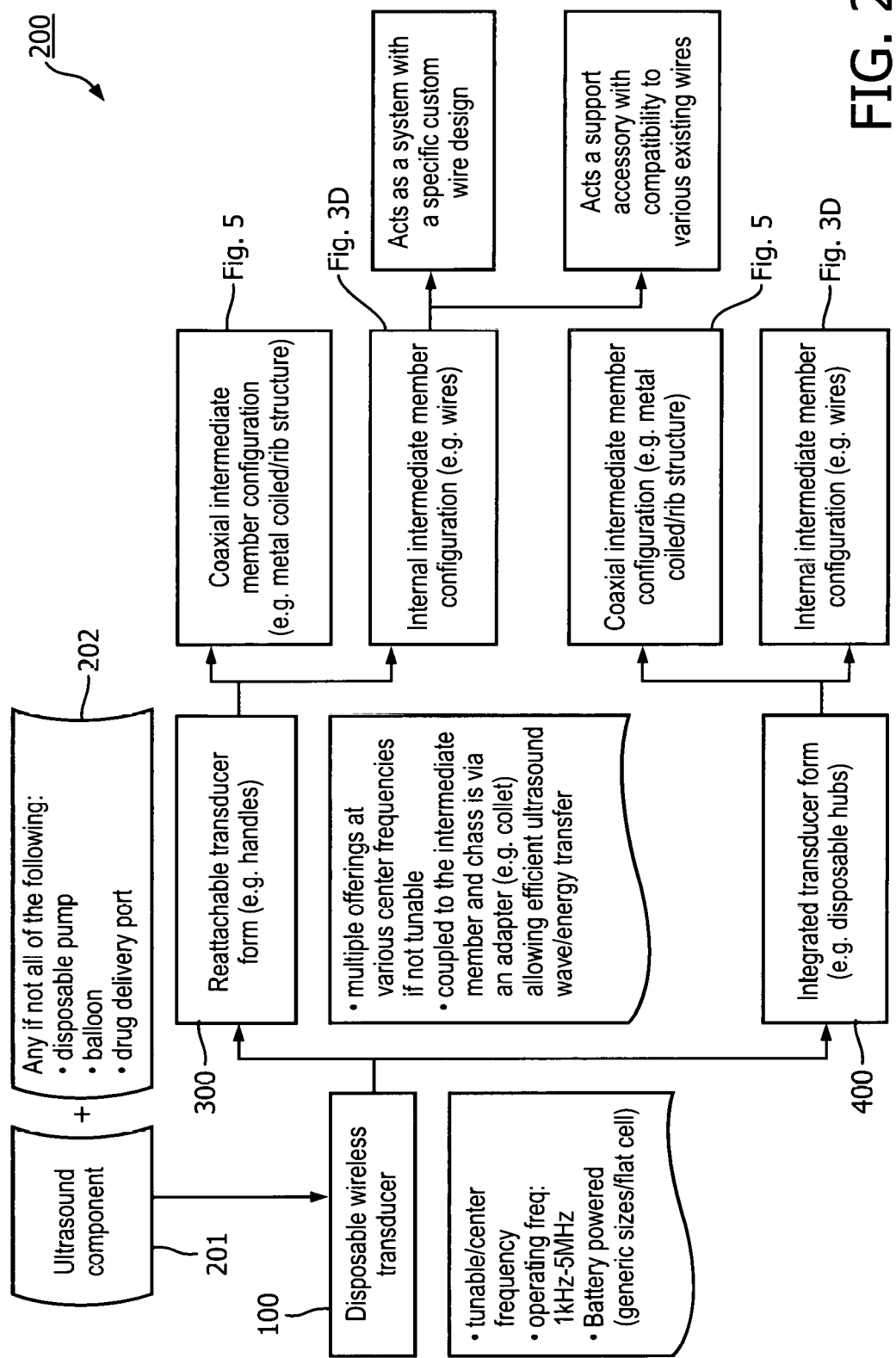
FIG. 2 is a diagram illustrating building blocks and optional features of a therapeutic ultrasound device according to some embodiments of the present disclosure.

Referring now to FIG. 2, shown therein is a diagram illustrating building blocks and optional features of a therapeutic ultrasound device according to varies aspects of the present disclosure. The embodiments of the present disclosure share a common scheme of combining an ultrasound component 201 with at least another interventional functionality 202 in a small-foot-print and disposable package. The at least another interventional functionality 202 can be a pump for drug delivery or aspiration, a balloon for balloon angioplasty, a drug delivery port, or an inflation line for an integrated percutaneous transluminal angioplasty (PTA) or peripheral cutting or drug coated balloon. The ultrasound component 201 can be a disposable wireless transducer 100, such as the therapeutic ultrasound device 100 shown in FIG. 1. The disposable wireless transducer 100 can be wireless (i.e. without connection to an external system) because it is self-contained, carrying with it a power source (i.e. a battery) and a signal source (a driving circuit, such as an ASIC) in a handheld housing. The therapeutic ultrasound device 100 (or disposable wireless transducer 100) has tunable center frequencies and can operate at center frequencies between 1 KHz and 5 MHz. The battery that powers the therapeutic ultrasound device 100 can be a flat-cell type battery and/or other suitable power source.

Figure 3C:
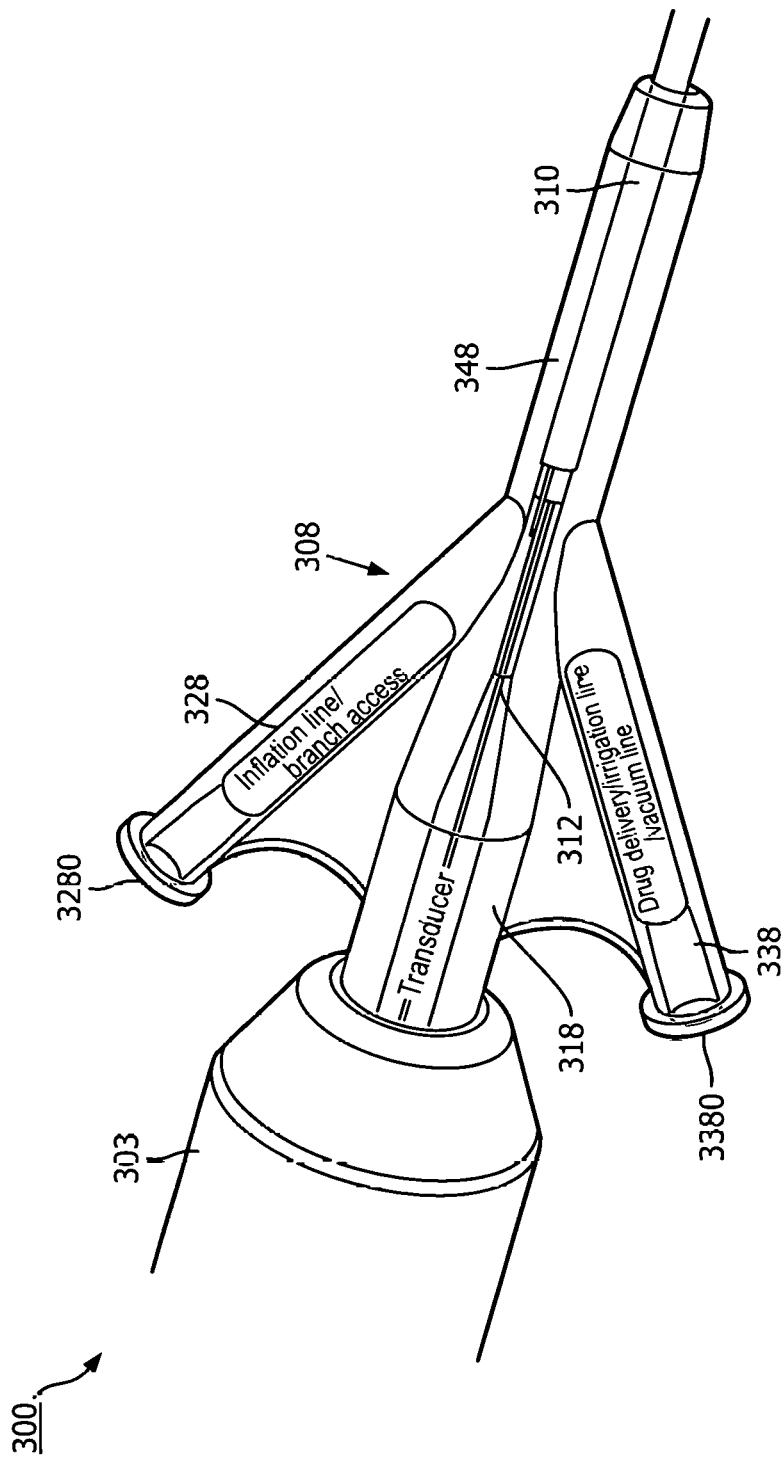
Figure 3D:
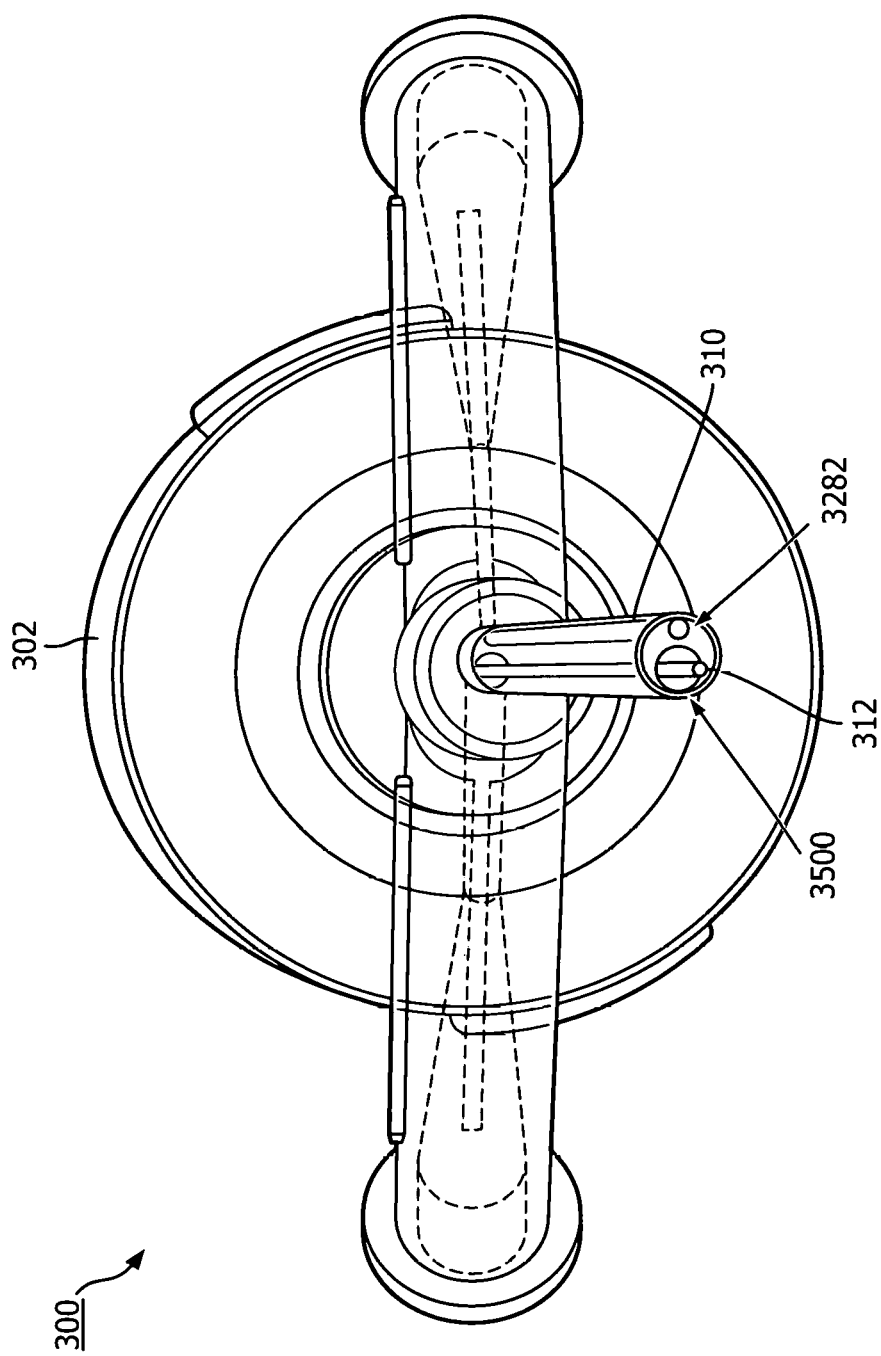
Figure 4:
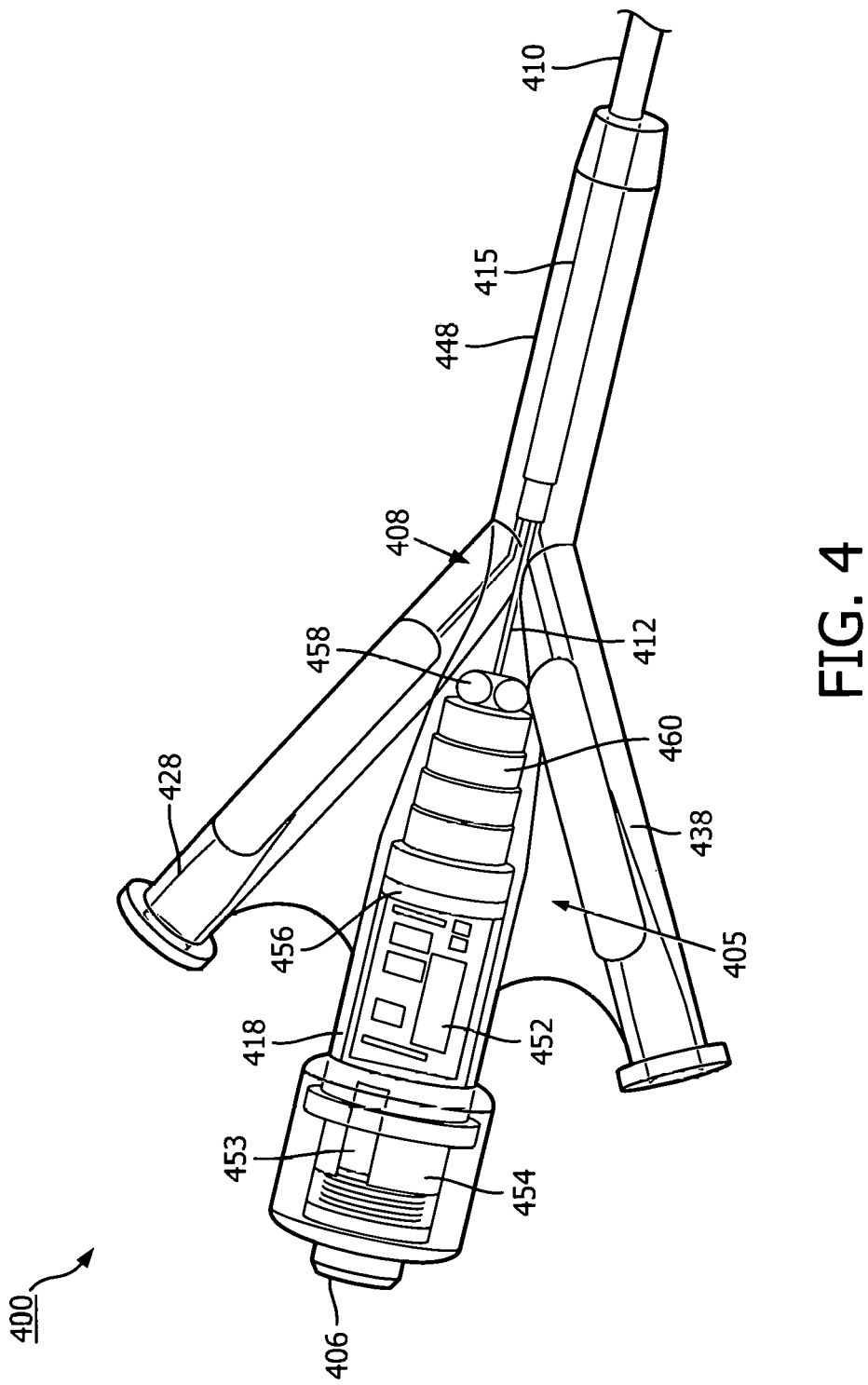
FIG. 4 is a diagrammatic schematic view of another therapeutic ultrasound device according to embodiments of the present disclosure.

The disposable wireless transducer 100 can take two forms—the reattachable transducer form, such as the therapeutic ultrasound device 300 in FIGS. 3A-3D and the integrated transducer form, such as the therapeutic ultrasound device 400 in FIG. 4. Although a single disposable wireless transducer 100 can have tunable center frequencies, the disposable wireless transducer 100 can come with different center frequencies or frequency ranges. For example, a first group of disposable wireless transducer 100 can have a 1 KHz center frequency, a second group of disposable wireless transducer 100 can have a 5 MHz center frequency, and a third group of disposable wireless transducer 100 can have a tunable 1 MHz to 3 MHz center frequency range. In some instances, each group of disposable wireless transducers can be color-coded for easy identification of operating frequencies or frequency ranges. The disposable wireless transducer 100 transmits ultrasound energy into a body lumen of a patient via an acoustic transmission member, which can also be referred to as an intermediate member, for example, if used to transmit ultrasound energy to a radiating member coupled to a distal end of the acoustic transmission member. At least one embodiment of the radiating member will be illustrated in FIG. 5 below. In some embodiments, at least a part of the proximal portion of the acoustic transmission member is coupled to the ultrasound assembly positioned within a housing. The acoustic transmission member is mechanically and/or acoustically coupled to the ultrasound assembly via a coupling component (or a couple mechanism), such as a collet head, a semi-free floating collet head, an O-ring, a clamp, and a keyed/lock mechanism. In case of the integrated form, one or more components of the device 100 are permanently coupled (e.g., a handle or housing, a flexible elongate member, an ultrasound assembly, an acoustic transmission member etc.) during the manufacturing process. In such instances, the entire device 100 will be disposed of after a single use. In the reattachable form, one or more components of the device 100 are reusable in multiple clinical procedures, while other components are discarded after a single use. For example, a single handle or housing and/or a single ultrasound assembly can be reused with multiple different flexible elongate members and/or acoustic transmission members, each of which may be discarded after a single use. In some embodiments, a battery harness of the integrated disposable wireless transducer 100 is structurally arranged for quick opening for easy removal and safe disposal of the battery.

Figure 5:
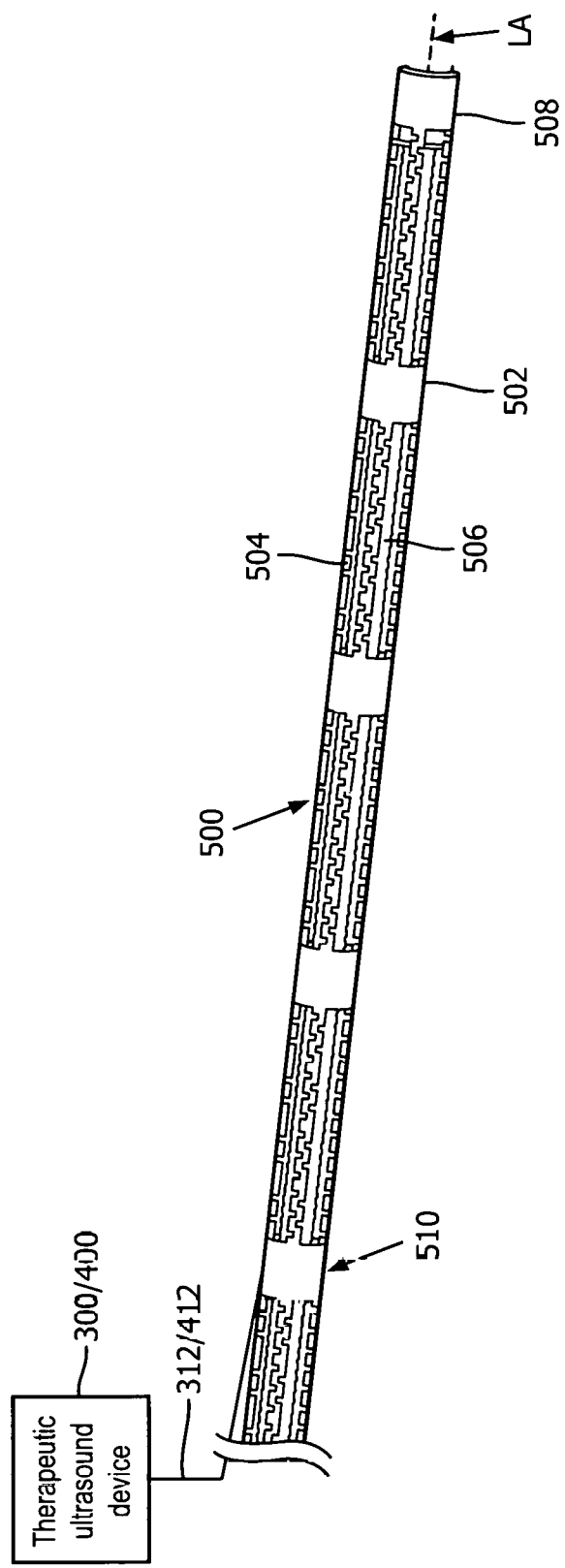
FIG. 5 is an enlarged diagrammatic schematic view of an acoustic transmission member of the therapeutic ultrasound device according to embodiments of the present disclosure.

In some embodiments, for both the reattachable and integrated forms of the disposable wireless transducer 100, the acoustic transmission member (or intermediate member) coupled to the ultrasound assembly can assume either a coaxial configuration, exemplarily shown in FIG. 5 or an internal configuration, exemplarily shown in FIG. 3D. In the coaxial configuration, the acoustic transmission member is coupled to a concentric structure that extends coaxially over the chassis of the delivery catheter. In some implementations, the coaxial configuration of the intermediate component geometry can be a thin walled super elastic alloy hypotube, various pitches of braided/coiled structures, and circumferential bands with rib(s) connecting it to the ultrasound assembly via the acoustic transmission member. In the internal configuration, the acoustic transmission member runs through a flexible elongate member. The internal configuration of the intermediate member can include a variety of geometries, such as tapered, grinded, laser cut, or otherwise machined wires or hypotubes. The intermediate member can be made of any suitable and biocompatible ultrasound medium material such as stainless steel, nitinol, and aluminum. Selection of the material should be based on maximization of ultrasound transmission efficiency in the desired frequency ranges and minimization of thickness of the intermediate member. In some instances, the therapeutic ultrasound device 100 of the reattachable form can serve as a system with a specific custom wire design or can be a support or secondary system with compatibility to various existing wires.

Referring now to FIG. 3A, shown therein is a therapeutic ultrasound device 300. The therapeutic ultrasound device 300 includes a handle (or housing) 302, a hub (or adaptor) 308, a flexible elongate member 310, and an acoustic transmission member 312. The handle 302 includes a proximal portion 301 and a distal portion 303. In embodiments represented in FIG. 3A, the hub 308 includes a proximal lumen 318, a distal lumen 348, a first access lumen 328, and a second access lumen 338. The flexible elongate member 310 can include more than one lumen that extends the entire length of the flexible elongate member 310. A proximal portion 315 of the flexible elongate member 310 is received within the distal lumen 348.

FIG. 3B illustrates a diagrammatic schematic view of the therapeutic ultrasound device 100 with the handle 302 opened up. In some embodiments, the handle 302 includes therewithin an ultrasound amplifier or horn 358, a piezoelectric transducer stack 360, a coupling mechanism 304, a backing plate 356, a driving circuit 352, a battery harness 354, and a switch 306. To operate the therapeutic ultrasound device 100, a user switches on the switch 306, closing the electrical circuit between in the battery harness 354 and the driving circuit 352. A battery 353 in the battery harness 354 powers the driving circuit to activate piezoelectric transducer stack 360 to generate ultrasound energy. The ultrasound energy generated by the piezoelectric transducer stack 360 is stabilized and/or amplified by the ultrasound horn 358 and transmitted via the acoustic transmission member 312 to the body lumen. In some instances, the driving circuit 352, the backing plate 356, the ultrasound amplifier 358, and/or other components described herein together can be referred to as the ultrasound assembly 305.

The piezoelectric transducer stack 360 includes a plurality of piezoelectric components. In some implementations, the plurality of piezoelectric components includes piezoelectric components with different thickness and dimensions and, therefore, different center frequencies. The device 300 can be a tunable ultrasound device to provide varying center frequencies of ultrasound energy by selectively activating one or more of the piezoelectric components of the stack 360. The piezoelectric transducer stack 360 may be positioned around a circumference of the ultrasound amplifier 358. The ultrasound amplifier 358 includes a through hole and the backing plate 356 includes a recess that is aligned with the through hole in the ultrasound amplifier 358. The acoustic transmission member 312 can be received within the through hole of the ultrasound amplifier 358 and the recess of the backing plate 356. In embodiments represented by FIG. 3B, the coupling mechanism 304 is positioned longitudinally between the ultrasound amplifier 358 and the backing plate 356. In some implementations, the coupling mechanism 304 can be a semi-free floating collet head, an O-ring, a clamp, or a keyed mechanical interface. The coupling mechanism 304 acoustically couples the acoustic transmission member 312 to the ultrasound assembly 305. The coupling mechanism 304 in the embodiment shown in FIGS. 3A and 3B is a collet head. In some implementations, the driving circuit 352 is an application specific integrated circuit (ASIC). The battery 353 can be a flat-cell type battery and/or other suitable power source. The switch 306 can be a button, a toggle, and/or other suitable user input device. At least a portion of the button extends through the housing 302 and the ultrasound assembly 305 can be activated by a push of the button.

In some embodiments, the hub 308, the acoustic transmission member 312, and/or the flexible elongate member 310 can be detached from the handle 302. Another hub, acoustic transmission member, and/or flexible elongate member 310 can be attached the same handle 302. In those embodiments, the hub 308, the acoustic transmission member 312, and/or the flexible elongate member 310 are disposable and can be referred to as the disposable hub. The handle 302 can be a reusable handle. For attachment of a disposable hub to the handle 302, a disposable hub is coupled to the handle 302 while the coupling mechanism 304 is left in an open position. After the disposable hub is securely coupled to the handle 302 and a proximal portion of the acoustic transmission member is received within the ultrasound amplifier and the backing plate, the coupling mechanism 304 is activated and turned to a closed position to acoustically couple the acoustic transmission member 312 to the ultrasound assembly 305. In some implementations, the ultrasound assembly 305 in the handle 302 operates at different center frequencies or different center frequency bands. For example, a first handle may operate at 1 KHz, a second handle at 5 MHz, and a third handle between 1 MHz and 3 MHz. In that example, the disposable portion can be selectively attached to one of the first, second and third handle for a favorable center frequency range that is suitable for the medical condition of the patient. In some instances, different handles of different center frequencies or different center frequency ranges can be switched while the flexible elongate member of a disposable hub remains within the patient's body lumen if a wide center frequency range is required for an operation.

Referring now to FIGS. 3C and 3D, shown therein are a perspective view and a distal view of the hub 308 of the therapeutic ultrasound device 100. In some embodiments, the acoustic transmission member 312 extends through the proximal lumen 318 and then into a first lumen 3500 within the proximal portion 315 of the flexible elongate member. In some implementations, the first access lumen 328 can be an inflation line or a branch access and include a port 3280. In some further implementations, the first access lumen 328 can be an inflation line for an integrated PTA/peripheral cutting/drug coated balloon. The second access lumen 338 can be a drug delivery line, an aspiration line, an irrigation line, or a vacuum line and include a port 3380. When serving as a drug delivery line or an aspiration line, the second access lumen 338 can be coupled to a pump. In some instances, the second access lumen 338 and the port 3380 are in fluid communication with the first lumen 3500 in which the acoustic transmission member 312 also extends. The first access lumen 328 and the port 3280 are in fluid communication with a second lumen 3282 extending within the flexible elongate member 310 and parallel to the first lumen 3500. While the embodiment shown in FIGS. 3A-3D does not require a guide wire, in some embodiments, the second lumen 3282 can serve as a guide wire lumen for the flexible elongate member 310 to ride on a guide wire. In some implementations, a radiopaque element may be incorporated into a distal portion of the flexible elongate member 310. With help of X-ray equipment, the radiopaque element allows a medical professional to determine whether the distal portion of the flexible elongate member 310 is positioned adjacent to a region of interest within a patient's body lumen.

FIG. 4 is a diagrammatic schematic view of another therapeutic ultrasound device 400 according to embodiments of the present disclosure. The therapeutic ultrasound device 400 include a housing 408, a flexible elongate member 410, and an acoustic transmission member 412. The housing includes therewithin an ultrasound amplifier 458, a piezoelectric transducer stack 460, a backing plate 456, a driving circuit 452, a battery harness 454, and a switch 406. The housing 408 includes a proximal lumen 418, a distal lumen 448, a first access lumen 428, and a second access lumen 438. The flexible elongate member 410 can include more than one lumen that extends the entire length of the flexible elongate member 410. A proximal portion 415 of the flexible elongate member 410 is received within the distal lumen 448. A battery 453 in the battery harness 454 powers the driving circuit 452 to activate piezoelectric transducer stack 460 to generate ultrasound energy. The ultrasound energy generated by the piezoelectric transducer stack 460 is amplified by the ultrasound amplifier 458 and transmitted via the acoustic transmission member 412 to a body lumen in which the flexible elongate member 410 is inserted. In some instances, the driving circuit 452, the backing plate 456, and the ultrasound amplifier 458 together can be referred to as the ultrasound assembly 405. Similar to the piezoelectric transducer stack 360 in FIG. 3B, the piezoelectric transducer stack 460 includes a plurality of piezoelectric components. In some implementations, the plurality of piezoelectric components includes piezoelectric components with different thickness and dimensions and, therefore, different center frequencies. The piezoelectric transducer stack 460 may be positioned around a circumference of the ultrasound amplifier 458. The ultrasound amplifier 458 includes a through hole and the backing plate 456 includes a recess that is aligned with the through hole in the ultrasound amplifier 458. The acoustic transmission member 412 can be received within the through hole of the ultrasound amplifier 458 and the recess of the backing plate 456 such that the acoustic transmission member 412 is acoustically coupled to the ultrasound assembly 405. In some implementations, the driving circuit 452 can be an ASIC. The battery 453 can be a flat-cell type battery and/or other suitable power source. The switch 406 can be a button, toggle, and/or other suitable user input device. At least a portion of the button extends through the housing 402 and the ultrasound assembly 405 can be activated by a push of the button.

The therapeutic ultrasound device 300 in FIG. 3A-3D includes a detachable disposable hub 308 while the therapeutic ultrasound device 400 in FIG. 4 does not include a counterpart. Instead, the proximal lumen 418 of the housing 408 houses the ultrasound amplifier 458, the piezoelectric transducer stack 460, the backing plate 456, the driving circuit 452, the battery harness 454, and the switch 406. The acoustic transmission member 412 is mechanically and/or acoustically coupled to the ultrasound assembly 405 during the manufacturing process. In some instances, the entire therapeutic ultrasound device 400 is disposable after a single use.

FIG. 5 is an enlarged diagrammatic schematic view of a radiating member 500 coupled to an acoustic transmission member, such as the acoustic transmission members 312 and 412. The acoustic transmission member 312/412 is coupled to a therapeutic ultrasound device, such as the therapeutic ultrasound devices 300 and 400. In some embodiments, a distal end of the acoustic transmission member 312/412 is coupled to a radiating member 500. In some embodiments, the radiating member 500 may be a part of a flexible elongate member, such as the flexible elongate members 310 and 410 and the acoustic transmission member 312/412 may be an inner member 506. The radiating member 500 is coaxially disposed about or around the inner member 506 along the longitudinal axis LA. As described further herein, the acoustic transmission member 312/412 operates to transmit ultrasound energy from the ultrasound assembly to the radiating member 500 and the radiating member 500 operates to deliver ultrasound therapeutic energy to the lumen 104 of the anatomy 102 at a frequency range between 1 KHz and 5 MHz for the purposes of treating an occlusion 106 observed therein. Accordingly, the radiating member 500 can be made out of any suitable and biocompatible ultrasound medium material that has a minimal wall thickness yet is sturdy and operable to deliver the ultrasound energy efficiently and safely at lower and higher end of the 1 KHz and 5 MHz frequency range. Examples of such materials include but are not limited to stainless steel, nitinol, and aluminum. The radiating member 500 is configured to radiate at one or more frequencies to emit ultrasound energy within the anatomy of the patient to deliver an ultrasound therapy. In some instance, the radiating member 500 may be a part of the acoustic transmission member 312/412.

As shown in FIG. 5, the geometry of an embodiment of the radiating member 500 may include a plurality of peripheral bands 502 spaced along the longitudinal axis LA. The bands 502 can extend circumferentially and/or annularly around the longitudinal axis LA. The bands 502 comprise a surface area that radiates ultrasound energy from the ultrasound assembly into the anatomy. Various embodiments of the radiating member 500 can include one or a plurality of bands 502. One or a plurality of elongated connecting members 504 may be interposed between the bands 502. The elongated connecting members 504 may be spaced apart at various radial or peripheral locations around the inner member 506. The connecting members 504 are configured to be flexible to allow the bands 502 to radiate/vibrate as needed to emit ultrasound energy from the ultrasound assembly. In another embodiment, the geometry of the radiating member 500 may include a thin walled super elastic alloy hypo tube, or various pitches of braided/coiled structures. The systems, devices, and methods of the present disclosure can include features described in U.S. Provisional Application No. 62/545,944, filed Aug. 15, 2017, the entirety of which is hereby incorporated by reference herein.

Figure 6:
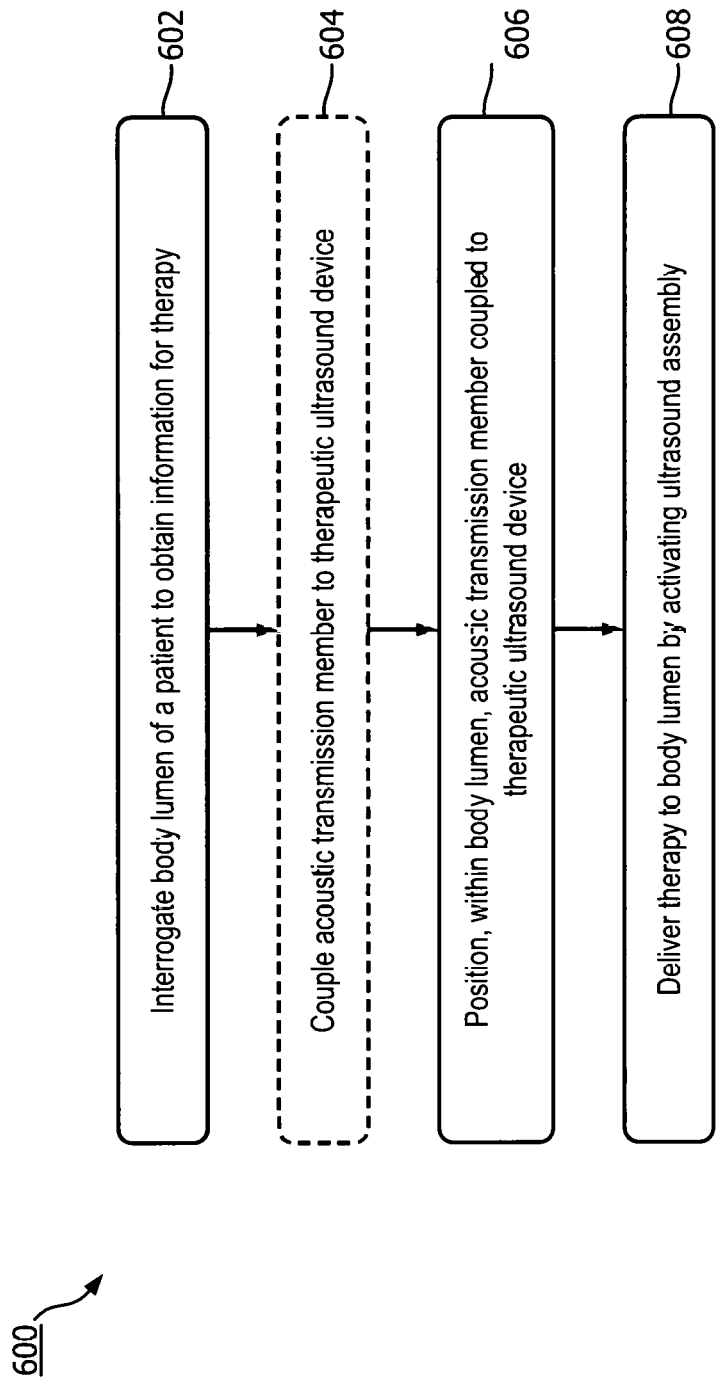
FIG. 6 is a flow diagram of a method of delivering therapeutic ultrasound to a body lumen of a patient according to embodiments of the present disclosure.

FIG. 6 is a flow diagram of a method 600 of delivering therapeutic ultrasound to a body lumen of a patient according to embodiments of the present disclosure. Method 600 begins at step 602 by interrogating a body lumen of a patient to obtain information for a therapy. In some embodiments, a diagnostic medical imaging device, such as x-ray imaging device or an intraluminal device (e.g., intravascular ultrasound (IVUS) imaging catheter, OCT imaging catheter, pressure and/or flow sensing guide wire) can be used to perform the operation of the step 602. In instances where the therapy is to be delivered to a target area or a region of interest, the medical imaging device should be positioned adjacent to the target area or region of interest and/or otherwise positioned to image the target area or region of interest.

At step 604, an acoustic transmission member is coupled to a therapeutic ultrasound device. The therapeutic ultrasound device may be similar to the therapeutic ultrasound device 300 in FIGS. 3A-3D. The therapeutic ultrasound device includes a housing and an ultrasound assembly positioned within the housing. The ultrasound assembly can include an ultrasound amplifier, a piezoelectric transducer stack positioned around the ultrasound amplifier, a backing plate, and a driving circuit. To perform the operation in step 604, the acoustic transmission member is threaded through a through hole in the ultrasound amplifier and into a recess in the backing plate. In some embodiments, the therapeutic ultrasound device may include a coupling mechanism (or a coupling component) that is positioned proximal to the backing plate. The coupling mechanism can mechanically and/or acoustically couple the acoustic transmission member to, e.g., the piezoelectric transducer stack, when the acoustic transmission member is received within the through hole of the ultrasound amplifier and the recess of the backing plate. In some instances, step 604 is an optional step. Step 604 may be needed if the reattachable form of the therapeutic ultrasound device, such as the therapeutic ultrasound device 300 in FIGS. 3A-3D, is used for the method 600. Step 604 may be omitted if the integrated form, such as the therapeutic ultrasound device 400 in FIG. 4, is used for the method 600 instead.

The method 600 proceeds to step 606. At step 606, the acoustic transmission member, which is coupled to the therapeutic ultrasound device, is positioned within the body lumen of the patient. In some embodiments, the acoustic transmission member is positioned within a lumen extending through a flexible elongate member coupled to the therapeutic ultrasound device. By positioning the flexible elongate member within the body lumen, the acoustic transmission member is also positioned within the body lumen. In some implementations, the acoustic transmission member itself delivers ultrasound energy to the body lumen. In some other implementations, a distal end of the acoustic transmission member is coupled to a radiating member, such as the radiating member 500 shown in FIG. 5, and the ultrasound energy is delivered to the body lumen by the radiating member.

At step 608 of the method 600, the therapy is delivered to the body lumen by activating the ultrasound assembly of the therapeutic ultrasound device. The therapeutic ultrasound device according to the present disclosure is wireless, self-powered, and self-contained. A battery in the housing powers the ultrasound assembly to generate ultrasound energy. In some embodiments, the housing of the therapeutic ultrasound device includes a switch, such as a push button. The ultrasound assembly can be activated by turning on the switch or pushing the push button. The ultrasound energy generated by the ultrasound assembly is then transmitted by the acoustic transmission member to the body lumen. In some instances, the delivery of the ultrasound energy is the therapy. In some other instances, the delivery of the ultrasound energy is a part of the therapy. For example, when the therapy is enhanced drug delivery, a pharmacological agent can be delivered to the body lumen before, after, or contemporaneous with delivery of ultrasound energy to the body lumen.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A therapeutic ultrasound device, comprising:
a housing configured for handheld operation by a user;
an ultrasound assembly positioned within the housing and configured to generate ultrasound energy, the ultrasound assembly comprising a backing plate;
a battery positioned in the housing and coupled to the ultrasound assembly to power the ultrasound assembly to generate the ultrasound energy;
a flexible elongate member configured to be positioned within a body of a patient, wherein the flexible elongate member comprises a proximal portion, a distal portion, and a first lumen extending between the proximal portion and the distal portion, wherein the housing is coupled to the proximal portion;
an acoustic transmission member comprising:
a proximal portion acoustically coupled to the ultrasound assembly and configured to receive the ultrasound energy, the proximal portion being partially received within a through hole of the backing plate; and
a distal portion extending within the first lumen and configured to transmit the ultrasound energy to the body to deliver a therapy; and
a coupling mechanism configured to acoustically couple the acoustic transmission member to the backing plate.

2. The therapeutic ultrasound device of claim 1, wherein the ultrasound assembly comprises a piezoelectric micromachined ultrasound transducer (PMUT), a capacitive micromachined ultrasound transducer (CMUT), a lead zirconate titanate (PZT) transducer, a PZT composite transducer, or a combination thereof.

3. The therapeutic ultrasound device of claim 1, wherein the ultrasound assembly comprises an ultrasound amplifier.

4. The therapeutic ultrasound device of claim 3,
wherein the backing plate is positioned proximal to the ultrasound amplifier,
wherein the proximal portion of the acoustic transmission member extends through a through hole within the ultrasound amplifier and is partially received within a recess in the backing plate, thereby acoustically coupled to the ultrasound assembly.

5. The therapeutic ultrasound device of claim 3, wherein the ultrasound assembly comprises a stack of a plurality of piezoelectric components positioned around a circumference of the ultrasound amplifier.

6. The therapeutic ultrasound device of claim 5, wherein each of the plurality of piezoelectric components is donut-shaped and includes a center frequency different from another of the plurality of piezoelectric components.

7. The therapeutic ultrasound device of claim 1, wherein the ultrasound assembly comprises a tunable center frequency range between 1 kHz and 5 MHz.

8. The therapeutic ultrasound device of claim 1, further comprising a switch positioned on the housing, wherein the switch is configured to, when switched on, turn on the ultrasound assembly.

9. The therapeutic ultrasound device of claim 1, wherein the housing further comprises a hub and is coupled to the proximal portion of the flexible elongate member via the hub.

10. The therapeutic ultrasound device of claim 9, further comprising:
a first access port coupled to the hub, the first access port comprising an access lumen in fluid communication with the first lumen of the flexible elongate member.

11. The therapeutic ultrasound device of claim 9, further comprising:
a second access port coupled to the hub, the second access port comprising an access lumen in fluid communication with a second lumen of the flexible elongate member, wherein the second lumen extends between the proximal portion and the distal portion of the flexible elongate member and parallel to the first lumen.

12. The therapeutic ultrasound device of claim 9, further comprising a coupling component proximal to the hub and configured to acoustically couple the acoustic transmission member.

13. The therapeutic ultrasound device of claim 12, wherein the coupling component comprises a collet head, an O-ring, a clamp, or a keyed interface.

14. A method for ultrasound therapy, comprising:
positioning, within a body of a patient, a flexible elongate member of a therapeutic intraluminal ultrasound device, the therapeutic intraluminal ultrasound device comprising:
a housing configured for handheld operation by a user,
an ultrasound assembly positioned within the housing and configured to generate ultrasound energy, the ultrasound assembly comprising a backing plate,
a battery positioned in the housing and coupled to the ultrasound assembly to power the ultrasound assembly to generate the ultrasound energy,
the flexible elongate member comprising a proximal portion, a distal portion, and a first lumen extending between the proximal portion and the distal portion, wherein the housing is coupled to the proximal portion,
an acoustic transmission member comprising a proximal portion acoustically coupled to the ultrasound assembly via a through hole of the backing plate and configured to receive the ultrasound energy, and a distal portion extending within the first lumen and configured to transmit the ultrasound energy to the body; and
a coupling mechanism configured to acoustically couple the acoustic transmission member to the backing plate; and
applying a therapy to the body of the patient by activating the ultrasound assembly.

15. The method of claim 14, wherein applying the therapy to the body of the patient comprises turning on a switch positioned on the housing of the therapeutic intraluminal ultrasound device.

16. The method of claim 14, further comprising:
prior to positioning, within the body of the patient, the flexible elongate member of the therapeutic intraluminal ultrasound device, interrogating the body with a diagnostic device to obtain information for the therapy.

17. The method of claim 14, further comprising:
prior to positioning, within the body of the patient, the flexible elongate member of the therapeutic intraluminal ultrasound device, coupling the acoustic transmission member to the ultrasound assembly.

* * * * *